United States Patent [19]

Nimberger

[11] Patent Number: 4,862,754

[45] Date of Patent: Sep. 5, 1989

[54] PORTABLE PISTON STYLE SAMPLE CYLINDER

[75] Inventor: Spencer M. Nimberger, Houston, Tex.

[73] Assignee: Precision General, Inc., Houston, Tex.

[21] Appl. No.: 291,755

[22] Filed: Dec. 29, 1988

Related U.S. Application Data

[63] Continuation-in-part of Ser. No. 131,622, Dec. 11, 1987, abandoned.

[51] Int. Cl.[4] ............................................. G01N 1/14
[52] U.S. Cl. .................................................. 73/864.62
[58] Field of Search ........... 73/864.61, 864.62, 864.63, 73/864.51, 863.81, 863.83, 863.84, 864.34, 863.71, 863.72, 864.91; 116/204; 277/125, 173, 177, 116.2; 366/129, 130, 140, 241, 267, 240

[56] References Cited

U.S. PATENT DOCUMENTS

| | | | |
|---|---|---|---|
| 2,857,184 | 10/1958 | Mancusi, Jr. | 277/173 |
| 3,389,603 | 6/1968 | Jacobs, III | 335/205 |
| 3,390,580 | 7/1968 | Taylor | 73/864.63 |
| 3,397,893 | 8/1968 | Kampert | 277/125 |
| 3,646,293 | 2/1972 | Howard | 335/207 |
| 3,789,670 | 2/1974 | Rosenwald . | |
| 3,793,888 | 2/1974 | Rosenwald . | |
| 3,892,130 | 7/1975 | Winget et al. | 73/864.62 |
| 4,409,850 | 10/1983 | Zeck | 73/864.62 |
| 4,459,865 | 7/1984 | Welker | 73/864.62 |
| 4,463,599 | 8/1984 | Welker | 73/864.62 |
| 4,536,758 | 8/1985 | Schweitzer, Jr. | 340/659 |
| 4,548,509 | 10/1985 | Parrott et al. . | |
| 4,584,887 | 4/1986 | Galen | 73/863.31 |
| 4,625,574 | 12/1986 | Robbins | 73/864.63 |

FOREIGN PATENT DOCUMENTS 404560 12/1943 Italy ................................ 116/227

OTHER PUBLICATIONS

Kwik Site Brochure, Portable Sample Vessels, YZ Industries.

Primary Examiner—Robert R. Raevis
Attorney, Agent, or Firm—Browning, Bushman, Zamecki & Anderson

[57] ABSTRACT

A piston-type portable sample cylinder is provided suitable for obtaining and transporting a liquified petroleum gas sample taken from a flow line. A piston slidable in a cylinder creates an increasing volume for the sample, and displaces an opposing inert gas maintained in the sample cylinder at a presesnt pressure. A toroidal mixing element has an outer diameter approximating the inner diameter of the cylinder, and slides over a cylinder projection on the piston to minimize voids when the sample cylinder is empty. The piston may be provided with a selectively adjustable seal for maintaining sealing integrity over a long life, with or without the use of lubricants. Magnets on the piston for activating external magnetic trip flags may be contained in a nylon protector ring. Precision fill measurements may be obtained from a sight gauge including a biased coiled tape mounted within the pressurized inert gas cavity of the sample cylinder and secured to one end of the piston.

20 Claims, 3 Drawing Sheets

PORTABLE PISTON STYLE SAMPLE CYLINDER

The present application is a continuation-in-part of U.S. Ser. No. 131,622 filed Dec. 11, 1987, now abandoned.

FIELD OF THE INVENTION

The present invention relates to vessels for collecting and transporting liquid or gas samples and, more particularly, relates to a pre-charged piston-type sample cylinder suitable for collecting and transporting liquified petroleum gas samples.

BACKGROUND OF THE INVENTION

Portable sample cylinders for collecting and transporting fluid samples are generally of the spun-end sample body variety or the piston-type sample cylinder variety. When sampling certain fluids, such as ethane, propane, butane, or other liquified petroleum gases (LPG), accurate sampling techniques require that the physical state of the fluid not change from the container (e.g., the LPG line) to the portable sample cylinder. Piston-type sample cylinders are thus generally preferred for sampling these fluids, since the sample can be input to the cylinder or vessel and maintained for subsequent analysis at the same pressure as the main container or fluid line. Moreover, a piston-type sample cylinder does not require that the sample be flushed through the cylinder, and thus only the precharged inert gas is released to either the atmosphere or a separate holding vessel.

The concentration of certain sample constituents within a portion of the sample cylinder may vary over time, yet a homogeneous sample fluid is required to perform accurate analysis on the sampled fluid. Various techniques have thus been devised for mixing the fluid in the sample cylinder prior to releasing the fluid from the cylinder for analysis. According to the plunger technique as disclosed in U.S. Pat. No. 3,793,888, an axially movable plunger is provided in the sample chamber for mixing the sample. This technique, however, is not preferred due to safety considerations, since the plunger is fully extended from the sample cylinder housing when the sample cylinder is full, and thereby creates shipping difficulties. Moreover, many gas samples are maintained at pressures within the cylinder such that the sampled gas behaves substantially as an incompressible fluid. Axial movement of the plunger into the cylinder reduces the effective volume of the sampled gas, further increasing its pressure and reducing its additional compressibility. Accordingly, the plunger may be difficult to compress, and thus considerable time is required to mix the sample.

Another variety of mixer for a sample cylinder utilizes a mixing ball movable by gravity in the sample chamber. This type of sample cylinder, as disclosed in U.S. Pat. No. 3,789,670, may be turned end-to-end for moving the mixing element from an end cap to the piston and back to the end cap. Voids within the sample chamber are preferably minimal, and accordingly the end cap and piston may be provided with a semi-spherical recess to jointly accomodate the mixing ball. In addition to the considerable manufacturing expense associated with providing the recesses, the mixing ball itself may act as a check valve, thereby preventing the sample from being discharged from the sample cylinder. Moreover, spherical balls do not function well to mix fluid in a cylindrical chamber, and thus again considerable time is required to mix the sample.

The seals on the piston in the sample cylinder are critical to the objective of obtaining a good sample. The sampled fluid must be kept isolated from the inert gas in the sample cylinder, and the inert gas must be kept isolated from the sampled fluid. The piston should sealingly move within the sample chamber under only a slight pressure differential. The use of conventional lubricants might minimize these problems, but such lubricants also absorb certain chemical groups in LPG, natural gas, or other samples, and are thus not recommended.

Ceramic magnets have been positioned on the piston of prior sample cylinders for activating external magnetic trip flags to obtain an indication of the position of the piston relative to the sample cylinder housing, and thus an indication of the sample volume. The magnets frequently shatter when impacted, however, causing significant damage to the interior wall of the sample cylinder and/or the seals or the piston, and may result in the loss of the sample when shattered pieces destroy the sealing effectiveness of the piston seals.

The above-described magnetic trip flag technique does not, however, provide an accurate reading of the sample quantity within the sample cylinder. Individual trip flags may be partially rather than fully turned, and thus the true position of the piston may vary $\frac{1}{4}''$ or more from the measured position, depending upon the reader. Inaccurate reading of the axial position of the piston in the sample cylinder may lead to a failure in recognizing a problem in the sampling procedure. For instance, if the sampling system is established to retrieve 50 cc of gas per day from a flow line and the system is checked after 3 days operation, the sample cylinder should indicate that 150 cc of sampled gas are in the cylinder. If, however, the sample reading is only 130 cc, the operator may assume the error lies in the accuracy of the indicator and thus assume the sample procedure is proper. On the other hand, if the operator is confident of the accuracy of the sample cylinder reading and the 130 cc reading is obtained, the operator will more thoroughly check the system and may discover, for example, that 20 cc pumped from the line to the sample cylinder was inadvertently lost due to a loose hose connection. In this case, the problem can thus be easily cured and the sample procedure accurately reinitiated.

Another variety of piston-type sample cylinder utilizes an indicator rod attached to the piston to relate the position of the piston and thus the sample quantity. This type of sample cylinder, as disclosed in U.S. Pat. No. 4,409,850, suffers from many of the safety and shipping problems associated with the plunger-type sample cylinder, since the indicator rod extends from the sampling housing. Also, it is time consuming to record the precise axial position of the rod with respect to the cylinder at various stages of the sampling process because marking or gradations on the rod would adversely affect the necessary sealing reliability between the end plate of the sample cylinder and the protruding rod.

Due in part to safety problems presented by a piston-type sample cylinder with an indicator rod or a plunger, prior art piston-type sample cylinders are generally shipped in a special container or "gun case" designed to protect the sample housing, related valves and gauges, and any rods or plungers extending from the housing. The containers themselves represent a considerable expense to the overall cost of obtaining and shipping samples, but have heretofore been considered necessary to fully protect the shipped sample.

The disadvantages of the prior art are overcome by the present invention, and an improved portable piston-type sample cylinder or vessel is hereinafter provided.

SUMMARY OF THE INVENTION

A piston-type portable sample cylinder is provided suitable for obtaining and transporting a fluid sample, such as LPG. The sample cylinder is initially precharged with an inert gas, which is then vented through a regulator, typically to atmosphere, as a sample fluid chamber increases. A toroidal mixing element having leading and trailing planar faces is provided in the sample chamber, and fits over a cylindrical projection on the piston for minimizing interior voids.

The piston of the sample cylinder includes selectively adjustable elastomeric-material seals for separating the sample fluid and the inert gas. The frictional force provided by the piston seals and thus the effectiveness of the seals may be easily altered by rotating an adjustment bolt on the piston. In one embodiment, the piston is provided with ceramic magnets for activating external magnetic trip flags. The magnets are cushioned to minimize shock and prevent fracture, and are housed within nylon rings to prevent magnet fragments from damaging the piston seals if fracture should occur.

In another embodiment of the invention, the position of the piston and thus the volume of the sample fluid in the sample cylinder, may be obtained by viewing a coil-type tape secured to the end of the piston. The tape is completely housed within the cavity filled with inert gas, and is visible through a sight glass. A magnetic strip or other device mounted on the tape may activate a switch to automatically terminate additional sample flow to the sample cylinder when the sample chamber is full.

These and further features and advantages of the present invention will become apparent from the following detailed description, wherein reference is made to the figures in the accompanying drawings.

DETAILED DESCRIPTION OF PREFERRED EMBODIMENTS

Figures 1, 2:
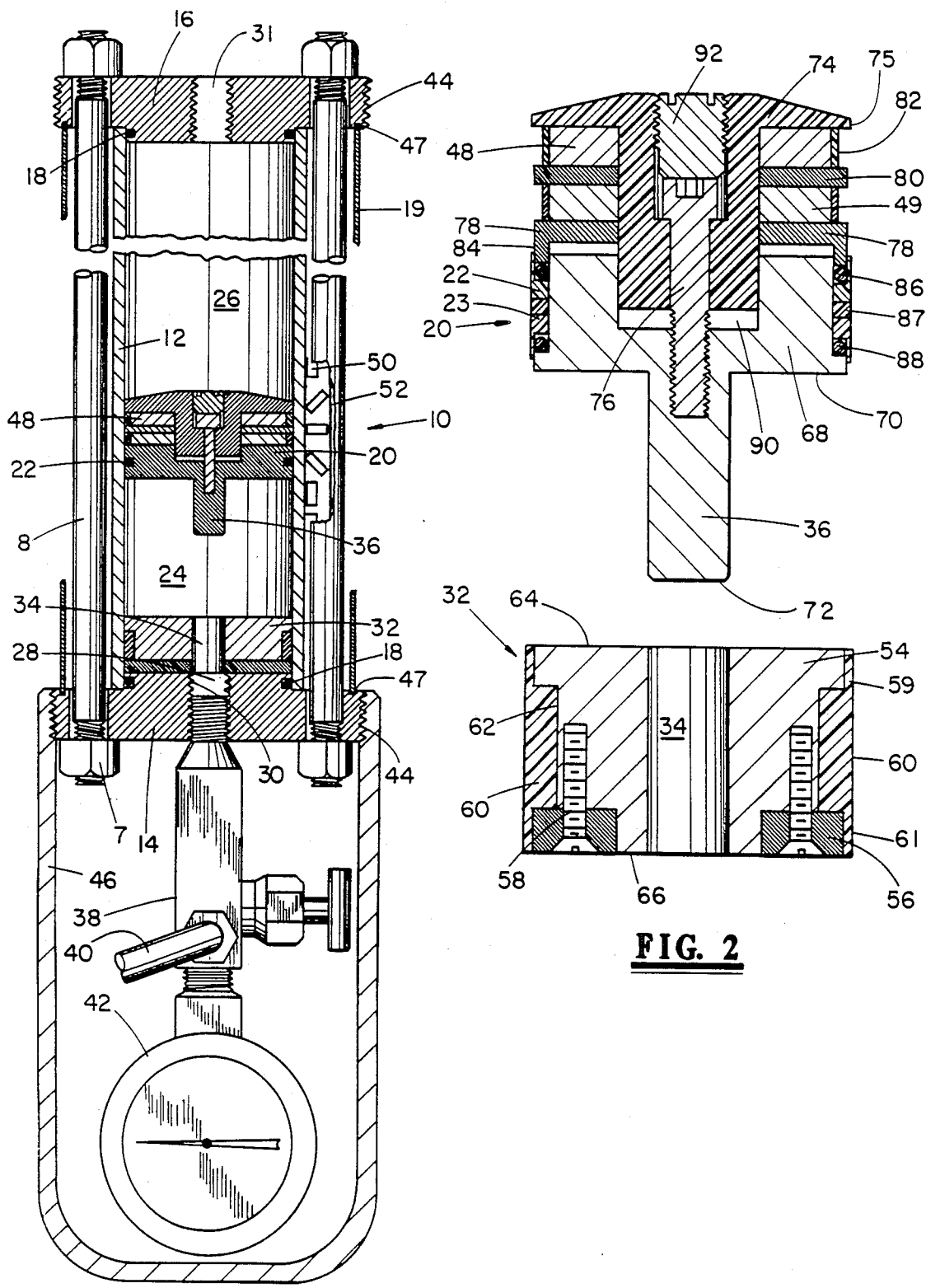
FIG. 1. is a pictorial view, aprtially in cross-section, of one embodiment of the sample cylinder in accordance with the present invention.
FIG. 2 is a detailed cross-sectional view of the psiton and mixing element shown in FIG. 1.

A portable sample cylinder 10 is depicted in FIG. 1 including a cylindrical tube 12 having a sample head or end cap 14 at one end of a charge head or end cap 16 at the other end. End caps 14 16 are secured in place by a plurality of rods 8 having nuts 7 at their threaded ends. The tube 12 and end caps 14, 16 are sealed by O rings 18 as shown. Piston 20 is slidably positioned within the tube 12, and carries a seal generally depicted at 22, which maintain a gas tight seal with the tube 12.

The tube, end caps, piston and seals as described above thus form a gas-tight sample chamber 24 and a gas-tight charge chamber 26 within the tube isolated from each other by the piston and piston seals. Fluid to be collected in the portable sample cylinder 10 enters chamber 24 through sample port 28 in the end cap 14, which is threaded at 30 for an NPT connection. The addition of fluid to chamber 24 moves piston 20 to expand chamber 24 and simultaneously contract chamber 26, which preferably contains a pressurized inert gas, e.g., nitrogen. Increased pressure in chamber 26 forces nitrogen out charge port 31 and through a pressure regulator in fluid communication therewith, discharging nitrogen to the atmosphere.

Toroidal mixing element 32 is free floating in chamber 24, and has an outer diameter only slightly less than the internal diameter of tube 12. A cylindrical-shaped passageway 34 through the mixer element 32 is similarly only slightly greater than the diameter of cylindrical-shaped projection 36 on piston 20, thereby minimizing voids in chamber 24 when the piston 20 and mixer 32 gravitate downward into engagement with end cap 14. Rotation of mixing element 32 relative to piston 20 thus has no adverse effect on the operation of the sample cylinder.

A conventional multi-port gauge valve 38 controls flow of fluid from a flow line 40 to chamber 24. Line 40, in turn, is typically connected to a fixed volume pump (not shown) and thence to a wellhead, line, or other container housing the fluid to be sampled. A standard pressure gauge 42 may be provided for measuring pressure in chamber 24. The outer flange portion of end cap 14 may be threaded at 44 for attaching a U-shaped metallic protector cap 46 which houses and thus protect the valve 38 and gauge 42 from damage.

Magnet 48 may be carried on piston 20 for turning trip flags 50 positioned within a conventional magnetic flag strip assembly 52 mounted external to the tube 12. The position of the trip flags 50 thus provides a technique for determining the approximate position of the piston 20 within the tube 12, and thus the quantity of sample fluid within the chamber 24 relative to its maximum sample volume.

Referring now to FIG. 2, a mixer element 32 is shown in greater detail, and comprises a stainless steel mixer body 54 which defines the diameter of the central passageway 34, and outer ring member 56 secured to body 54 by conventional bolts 58, and a nylon sleeve-shaped guide 60. A recess 62 in body 54 thus allows the guide 60 to be sandwiched between the body 54 and the outer ring 56, as shown. The thinner piston-directed extension 59 and end cap-directed extension 61 provide additional areas for sliding engagement with the inner wall of cylinder 12, and prevent the body 54 and ring member 56 from engaging the cylinder 12. End surfaces 64 and 66 of mixer 34 are each planar and perpendicular to the axis of tube 12. The outer diameter of guide 60 is slightly greater than the outer diameter of the body 54 or the outer ring member 56, and is only slightly less than the internal diameter of tube 12, as explained above. Accordingly, substantially all fluid passes through passageway 34 when mixer element 32 moves within the chamber 24, and little fluid passes between the mixer element 32 and the tube 12.

The preferred diameter of passageway 34, and thus approximately the diameter of projection 36, is a function of the viscosity of the sampled fluid, the specific gravity of the mixing element 32, and the desired velocity of the mixing element as it falls by gravity within the chamber 24 and toward either the piston 20 or the end cap 14. The desired vertical velocity of the mixing element is in the range of from 0.3 to 1.0 ft/sec, which is sufficient to allow the operator to audibly detect or "feel" the mixing element engage the end cap. For mixing liquids having a viscocity approximating that of water, the preferred passageway diameter 34 is in the range of from 20% to 35% of the inner diameter of the cylinder 12. For mixing gasses, the preferred passageway diameter is in the range of from 5% to 15% of the inner diameter of the cylinder 12. This substantially reduced passageway diameter for the mixing element when used with gasses both controls the falling rate of the mixing element, as noted above, and creates a desired "jet action" as the gas is forced at a high velocity through the falling mixing element.

The mixer element 34 disclosed herein provides a comparatively inexpensive technique for easily, quickly and reliably obtaining a homogeneous mixture of sample within the chamber 24. The action of forcing fluid through the passageway of the mixer element is substantially more efficient at mixing the fluid than passing a ball through the fluid. It should be understood, of course, that a slight amount of fluid may pass between the guide 60 and the interior diameter of the tube 12, and/or between the projection 36 on the piston and the inner diameter of the passageway through the body 54, so that a "fluid lock" situation cannot develop between the mixer element 32 and the combination of the tube 12 and the piston 20.

Piston 20 comprises a generally Y-shaped body 68, with its axially positioned cylindrical portion 36 adapted for fitting within the passageway 34, and planar surface 70 adapted for engagement with surface 64 to minimize voids. The length of projection 36 will be substantially identical to the axial space between surfaces 64 and 66, and accordingly the planar end surface 72 of projection 36 will be axially aligned with the surface 66 when surfaces 64 and 70 are in engagement.

End cap 74 is secured to body 68, yet is axially positionable with respect to body 68 by allen bolt 76, as shown in FIG. 2. A toroidal clamping ring 78 is slidably positioned on end cap 74, an axially compresses a pair of ceramic ring-shaped magnets 48, 49 separated by a carbond steel washer 80, which serves as a magnet intensifier for more reliably tripping flags 50 in response to the position of the magnets relative to the external trip flags. The magnets 48, 49 are thus not loosely mounted on the piston body, but rather are secured under the compressive force of bolt 76 into rigid engagement with both the end cap 74 and the piston body 68. By mounting the magnets under compression in rigid engagement with the end cap and piston body, the likelihood of shock damage to the magnets is substantially reduced.

Magnets 48, 49 are also somewhat protected from shock damage by a pair of nylon protector rings 82, each of which has a sleeve-like configuration. Nevertheless, the possibility exists that one or both of the magnets could fracture. According to the present invention, the nylon protector rings 82 fully encapsulates the magnets 48, 49. Each magnet is thus enclosed by its respective nylon protector ring, the cylindrical surface of end cap 74, and the planar end surface of either end cap 74 or ring 78. Even if the magnet should fracture, magnet fragments will be contained within protector ring 82, and accordingly cannot damage the piston seals 22 or other components of the sample cylinder. The sleeve-shaped rings 82 do not serve to mount or secure the magnets 48, 49 to the piston 20 since, as previously explained, this function is obtained by bolt 76 compressing the magnets into rigid sandwiched engagement with the end cap 74 and the piston body 68. Rather, the rings 82 serve to keep magnet fragments from damaging the piston seals 22 and/or the inner cylindrical surface of the cylinder tube 12.

An annular lip 84 on ring 78 is shown in engagement with O-ring 86, and simultaneously exerts a substantially identical compressive force on O-rings 86 and 88 as bolt 76 brings end cap 74 and ring 78 axially closer to body 68. A pair of polytetrafluoroethylene sealing rings 22, 23, each having a generally L-shaped cross-sectional configuration, are sandwiched between O-rings 86 and 88 as shown. The leg of seal 22 is directed toward the chamber 26 and thus seal 22 primarily serves to seal nitrogen from chamber 24. The leg of seal 23 is oppositely directed to chamber 24 and thus seals sample fluid from chamber 26. The sealing effectiveness of seals 22, 23 is thus responsive to the pressure in chambers 26 and 24, respectively.

Compression of O-rings 86 and 88 flexes the leg portion of each seal radially outward, thereby increasing the effectiveness of the seal. A spacing 90 between end cap 74 and body 68 thus allows for sufficient axial movement of ring 78 relative to body 68 to exert a selected amount of compressive force on O-rings 86 and 88. An opening in the end cap 74 for obtaining access to bolt 76 may be filled with a standard set screw 92, which prevents inadvertent rotation of bolt 76 due to vibration.

End cap 74 may be fabricated from an elastomeric material, such as Delrin, so that end surface 75 will slidably engage the cylinder 12 and serve to maintain the piston in axial alignment with the cylinder. A similar guiding action may be obtained from elastomeric ring 87, which is axially movable on the body 68 and sandwiched between seals 22 and 23, as shown. The outer cylindrical surface 75 and the outer surface of ring member 87 are thus axially spaced and together provide the desired guiding action which maintains the piston aligned with the cylinder. These members are not, however, intended to sealingly engage the cylinder, since that function is obtained by seals 22, 23 previously described.

According to the present invention, the sealing effectiveness of both seals 22, 23 can be easily adjusted uniformly around the periphery of the piston by rotating a single bolt 76 to bring end cap 74 and clamping ring 78 axially toward or away from the piston body 68. The polytetrafluoroethylene seals 22, 23 provide low frictional resistance, and the desired compressive force on O-rings 86 and 88 may be obtained by removing end cap 16 and observing the sliding movement of piston 20 in tube 12.

Figure 3:
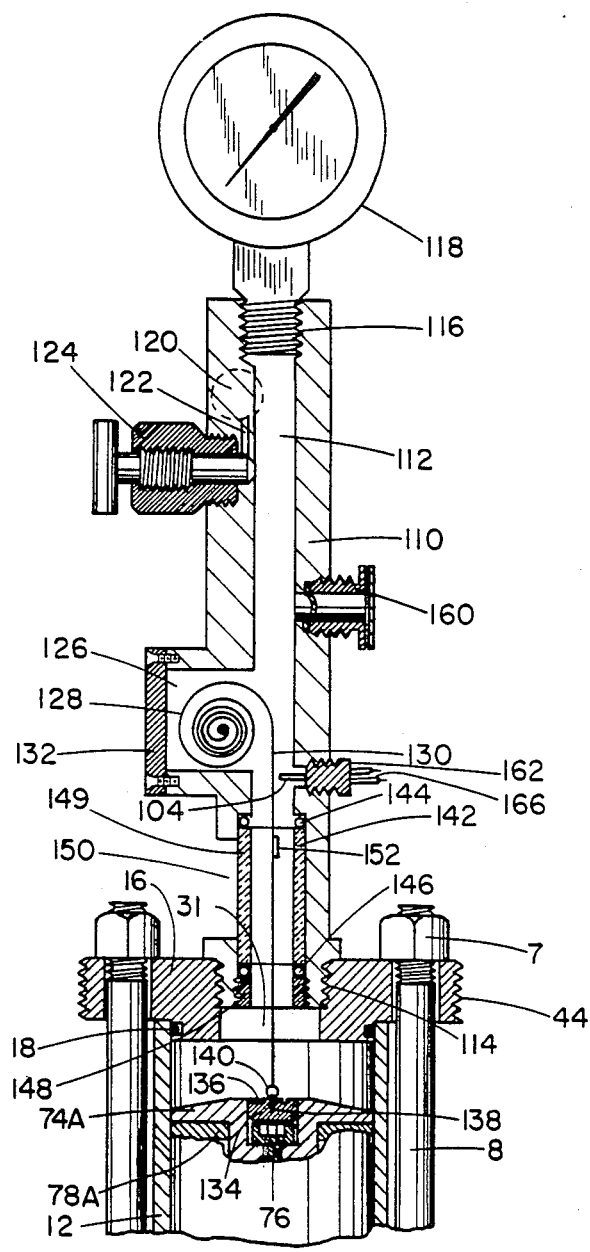
FIG. 3 depicts an alternate embodiment of the sample cylinder shown in FIG. 1, including a coiled tape precision fill indicator.

FIG. 3 depicts an alternate embodiment of the present invention, in which the accuracy of the technique for determining the quantity of sample fluid in the sample cylinder has been significantly increased compared to the magnetic trip flag technique previously described. In FIG. 3, nuts 7, rods 8, tube 12, end cap 16, seals 18 and the components not depicted are of the type previously described. The end cap 74A of piston 20A engages clamping ring 78A, since the magnets on the piston are not required.

Housing 110 having a central passageway 112 is provided with NPT threads 114 for sealing engagement with the mating threads of port 32. The opposite end of body 110 is similarly provided with NPT threads 116 for receiving pressure gauge 118. Nitrogen input and output port 120 in body 110 is in communication with passageway 112 via passageway 122, which may be closed off by a valve stem and bonnet assembly 124. Port 120, in turn, is in fluid communication with an adjustable regulator (not shown) for automatically venting nitrogen from chamber 26 to the atmosphere in response to a build up of pressure beyond the regulated limit. A standard pressure relief disk 160 is also mounted on the body 110 and is in communication with passageway 112, and pressure on either side of the piston is prevented from increasing beyond an acceptable limit.

Body 110 is also provided with cavity 126 open to chamber 26 and sealed from the atmosphere by cover 132. Metallic coil 128 of the type conventionally used in a tape measurer is housed within cavity 126 with the axis of the coil 128 secured to the body 110 in a conventional manner. Tape 130 extends through the passageway 112 substantially along the axis of tube 12, and is secured to set screw 134 in end cap 74A by a screw 138 and swivel 140. Set screw 134 contains one or more radially offset apertures or slots 136 for facilitating threaded engagement in the end cap 74A while preferably enabling the tape 130 to remain axially aligned with the tube 12.

A sleeve-shaped plexiglass sight member 149 has sealing O-rings 144 and 146 at each end, and is sandwiched between body 110 and securing member 148 as shown. Member 148 may have an internal surface adapted for fitting engagement with an allen wrench or other suitable tool so that member 148 can be axially threaded along body 110 to compress the O-rings 144 and 146 to sufficient to effect a gas-tight seal. Body 110 circumferentially encloses all but a thin elongate portion 150 of the sight glass, which portion is exposed for viewing the axial position of tape 130.

Tape 130 is provided with standard tape markings or gradations, and thus visibly depicts either the volume of supply fluid in the sample chamber or the axial position of the piston 30 relative to the tube 12. Tape 130 is thus calibrated according to standard techniques, so that the viewer can easily and reliably obtain a precise measurement of the position of the piston at any point in time. If desired, a small magnetic disk 152 or other suitable activating device may be fixed at a selected location along tape 130 for automatically activating a sensor 162 having a probe 164 projecting into the passageway 112 as disk 152 moves axially past the sensor. The sensor 162, in turn, may be connected by wires 166 to an alarm device (not shown) for warning the operator that the sample chamber 24 has reached a preselected volume, e.g., 80% of its maximum capacity. Alternatively, the sensor 162 could be connected to the pump used to supply sample fluid to port 28, thereby automatically shutting off the further supply of fluid to the sample cylinder.

The technique for using the sample cylinder of the present invention will now be briefly described. Referring to FIGS. 1 and 3, the sample cylinder will be typically be shipped from a laboratory to the test site, e.g., an LPG line, with the sample cylinder empty. Piston 20 and mixing element 32 will thus be forced against the end cap 14 by nitrogen pressure in chamber 26. Generally chamber 26 would thus typically be pre-charged at a pressure slightly in excess of the known or presumed pressure in the LPG line to be tested.

Once line 40 is connected to a positive displacement pump and to the LPG line, the exact pressure to the LPG line may be read, and the regulator connected to discharge port 32 set at that pressure, thereby pressure balancing the piston 20. With gauge valve 38 open, fluid may be transmitted from the LPG line to the sample cylinder in an incremental manner, according to standard techniques. It may be seen that fluid pressure acts initially on projection 36 of the piston 20, so that the mixing element cannot serve to block fluid to or from the sample cylinder. As the piston 20 moves toward the end cap 16, a slight increase in fluid pressure in chamber 26 will automatically cause nitrogen to vent through port 32 through the regulator and then to the atmosphere or an inert gas retaining vessel (not shown).

At any time during the fluid sampling operation, the operator may easily and accurately detect the position of the piston 20 within the tube 12, and thus the quantity of fluid in the sample cylinder. If desired, the sampling operation may be terminated or an audio or visual warning device initiated when member 152 passes sensor 162, thereby indicating that the sample quantity has reached a predetermined amount. If the trip flag/piston magnet embodiment is used, the sleeves 82 contain any magnet fragments (should they fracture), thereby minimizing or eliminating the likelihood that the fragments will damage the seals 22.

Once the desired sample has been obtained and the valves 38 and 124 closed, the sample cylinder may be shipped with U-shaped metallic protector caps 46 threaded to each of the end caps 14, 16. The valves and gauges at each end of the sample cylinder will thus be suitably protected for shipment by protector caps 46, and the expense of a "gun case" is not required. Moreover, no elongate members protrude from the sample cylinder, and thus problems associated with such prior art sample cylinders are avoided. Once the sample cylinder reaches the lab and the fluid sample is to be withdrawn, the sample cylinder may be easily tilted end-to-end to move mixing element 32 in chamber 24 by gravity, thereby effectively mixing the sample. Sample fluid may thereafter be released from the sample cylinder by opening valve 38, with mixing element 34 being incapable of unintentionally sealing off port 28.

Further protection of the sample cylinder during shipment may be obtained by providing a sleeve-like metallic protector case 19 for enclosing the cylinder 12 and the rods 8. As shown in FIG. 1, opposing circular grooves 47 may be provided in the inner faces of end caps 14, 16, with each groove 47 adapted to receive an end of protector tube 19. As the sample cylinder is assembled, the tube 49 may thus be aligned for fitting in both grooves 47 as the bolts 7 are tightened. Sealing engagement between the end caps and tube 19 is not required although, if desired, the annulus between tube 19 and cylinder 12 may be filled with a suitable insulation to better maintain the temperature of the collected sample during shipment at its collected temperature. The combination of the tube 19 and end caps 46 thus protect the cylinder 12 and the valve and gauge assemblies at each end of the cylinder.

Once the sample has been discharged from the sampler, the operator may remove end cap 16 and observe the piston movement in the tube 12. If desired, increased or decreased sealing effectiveness can easily be obtained by removing set screw 90, by then rotating bolt 76, thereby compressing or releasing O-rings 86 and 88, and accordingly moving the legs slightly outward or inward on seals 22 and 23, as previously described. Once the desired sealing effectiveness of the piston seals has been obtained, the sample cylinder may be refilled with nitrogen in chamber 26, and sent to the field for another sampling operation.

One of the advantages of the piston sealing arrangement depicted in FIG. 2 is that the piston can be easily removed from and inserted into the cylinder 12 without damaging piston seals 22, 23. When in their sealing position, the outer sealing surfaces of sealing members 22, 23 must be equal to or greater in diameter than the outer diameter of guide ring 87. If the piston is to be removed from the cylinder and subsequently replaced after checking the seals, bolt 76 may be unthreaded to reduce or eliminate the axially compressive force on O-rings 86, 88, thereby relaxing the outer force on the legs of the sealing elements and effectively reducing the outer diameter of the seals to a dimension less than the outer diameter of end cap 74 and ring 87. Once safely reinserted in the cylinder 122, the bolt 76 may be tightened to again radially move the sealing elements outwardly into sealed engagement with the cylinder.

Figure 4:
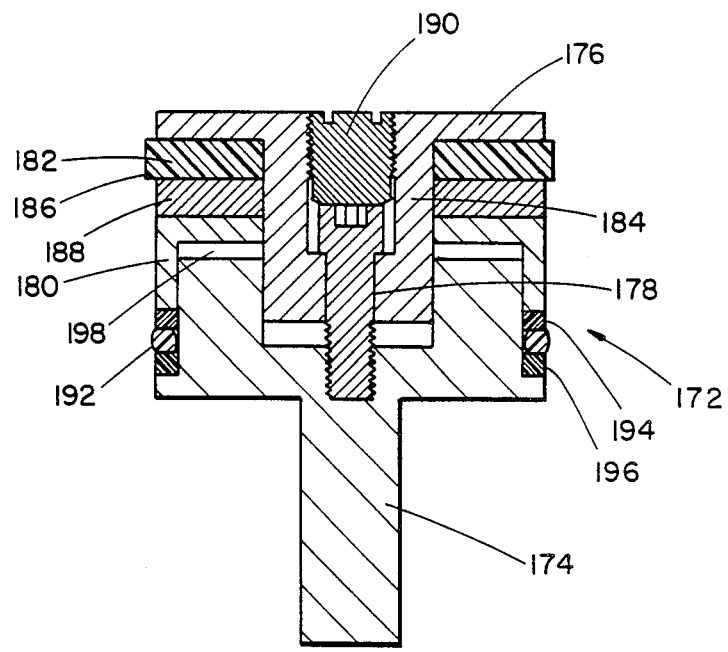
FIG. 4 depicts a cross-sectional view of another embodiment of the piston shown in FIG. 2.

Another embodiment of a piston assembly 172 is shown in FIG. 4, which includes a generally Y-shaped body 174 as previously discussed. End cap 176 is axially positioned with respect to body 174 by allen bolt 178, and clamping ring 180 is slidably positioned on the end cap.

End cap 176 may be fabricated from metal and no longer engages the inner surface of cylinder 12. Rather, that function has been replaced by an elastomeric-material washer 182, which has an internal diameter only slightly greater than the external diameter of cylindrical portion 184 of end cap 176, and has an external cylindrical surface 186 which serves to maintain the piston 172 in axial alignment with the cylinder 12. Also, the pair of spaced magnets are replaced by steel washer member 188 secured under the compressive force of the bolt 178 into rigid engagement with the end cap 176 between the washer 182 and the clamping ring 180. While other components of the piston 172 maybe fabricated of metal, such as stainless steel or a similar non-metallic metal, the mass and composition of the steel washer 188 enables a magnet external of the cylinder 12 to be sufficiently responsive to ring 188 such that an operator can use such a magnet to approximately locate the axial position of the steel member 188 and thus determine the axial position of the piston within the cylinder 12.

As with the embodiment of the piston previously discussed, the ring 180 exerts axially-directed compressive force on the piston sealing member, which force may be adjusted by removing plug 190 and rotating the bolt 178 relative to the body 174. In FIG. 4, however, the pair of sealing members previously discussed are replaced by a single O-ring sealing member 192, which is sandwiched between a pair of elastomeric-material back up rings 194, 196 each having a diameter equal to the diameter 186 of washer 182. Spacing 198 allows sufficient axial movement of ring 180 to exert a selected amount of compressive force on the O-ring 192. During use, the elastomeric-material washer 182, the backup rings 194 and 196, and O-ring 192 are thus the only components of the piston shown in FIG. 4 which engage the inner sidewalls of cylinder 12. Back up rings 194 and 196 enable the compressive force of the bolt 178 acting through 180 to give the sealing O-ring 192 an almost rectangular cross-sectional configuration, and prevent the O-ring from axially "flowing" under pressure between either the back up rings and the surface 12 or body 174, thereby maintaining the useful life of the O-rings. The O-ring 192 thus provides sealing engagement between the cylinder 12 and the body 174 of the piston shown in FIG. 4, although the O-ring is not fluid-pressure responsive as are the sealing members for the piston assembly shown in FIG. 2.

Various other embodiments of the piston assembly are contemplated by and within the scope of the present invention. The sealing member shown in FIG. 2 may be used with the piston otherwise depicted in FIG. 4, and the steel washer 188 shown in FIG. 4 may be used instead of the magnets for the piston otherwise depicted in FIG. 2. The O-rings 86, 88 and/or 182 may be replaced by other conventional sealing members, such as a polytetrafluoroethylene-material sealing member having a generally rectangular cross-sectional configuration and sufficiently axially compressible to expand radially into sealing engagement with the cylinder 12. The piston sealing members may be "non-adjustable", in which case a conventional bolt may simply secure the end cap into fixed engagement with the piston body. If a mixing element as shown in FIG. 2 is not utilized as part of the sample cylinder assembly, the piston body projection 36 is not required, so that surface 70 of the piston body as shown in FIG. 2 could engage the end cap 14 and thereby eliminate voids within the cylinder. Finally, various mechanisms other than a bolt may be used to selectively adjust the axial position of the end cap relative to the piston body and thereby adjust the axially-directed force on the piston sealing member to expand the sealing member radially outward and thereby increase its sealing effectiveness with the cylinder 12. For example, the conventional coil spring member (not depicted) may be provided between the head of bolt 76 as shown in FIG. 2 and the end of cap 74 adjacent to spacing 90. In this embodiment, the bolt 76 would still allow the axially-directed force on the piston sealing member to be adjusted, however the spring would allow movement of the ring 78 with respect to the body 68 to accomodate wear of the sealing member and maintain sealing integrity over a lengthy period of time without adjustment by the bolt 78.

Other than the visual piston position (sample volume) measurement technique utilizing marking on the tape as described above, alternative piston position measurement techniques utilizing the coiled or uncoiled length of the tape are within the scope of the present invention. For example, a photoelectric sensor may be provided for outputting a signal as each marking on the tape passes the sensor, thereby "counting" the markings and providing an accurate output indicative of the position of the piston. Also, axial movement of the tape as the piston moves may drive a mechanical or electrical counter mounted on the housing 110 for a similar purpose. As a further example, notches could be provided in the tape or small "fingers" added to the tape at regularly established intervals for activating standard reed switches or other counters. Regardless of the exact measurement technique used, it is a feature of the present invention that the piston position be inexpensively yet reliably determined by a sensor functionally extending into a pressurized cavity in fluid communication with chamber 26. This feature of the invention also enables the output from the measurement sensor to be easily digitized and transmitted to a remotely positioned station by conventional telemetry techniques. Accordingly, a central station operation can reliably monitor the sampled volume of various sample cylinders according to the present invention each positioned at different remote locations.

Various embodiments should now be apparent and should be understood as being within the scope of the present invention. For example, the passageway through the mixing element and thus the configuration of the projection on the piston need not be cylindrical, and a conical passageway and an approximately configured projection on the piston may be employed. In the embodiment shown in FIG. 3, the end cap 74A and ring 78A may be fabricated as a unitary piece. Rather than encapsulate the magnets between the end cap 74 and sleeves 82, the exterior surfaces of each magnet 48, 49 may be coated with a thermoplastic coating which permanently seals the magnets. It should be understood that item 152 need not be coiled within the tape 128, and accordingly need not be flexible. Various fluids other than nitrogen could be used within the pressurized chamber for the precharging effect, although an inert gas releasable to the atmosphere is preferred.

The term "fluid" as used herein should be understood to include gasses, liquids, and mixtures of gasses and liquids under various pressures. The term "elastomeric" as used herein is intended to encompass the terms plastic, thermoplastic, and similar terms indicative of high elasticity, and further includes materials such as nylon, Delrin, polytetrafluoroethylene, and PEEK.

Although the invention has been described in terms of the specified embodiments which are set forth in detail, it should thus be understood that this is by illustration only and that the invention is not necessarily limited thereto, since other alternative embodiments and operating techniques will become apparent to those skilled in the art in view of the disclosure. Accordingly, modifications are contemplated which can be made without departing from the spirit of the described invention.

What is claimed is:

1. A portable sample cylinder for collecting and transporting a fluid sample, including a cylindrical tube having an interior surface with an inner diameter and defining a sample cylinder axis, a sample end cap at one end of the tube and a charge end cap at the other end of the tube, a piston having a sample facing surface and a charge facing surface and slidable within the tube for defining a sample chamber between the sample end cap and the piston, and a charge chamber between the charge end cap and the piston, a sample input port for introducing the fluid sample to the sample chamber, and a charge port for inputting and releasing fluid from the charge chamber, the sample cylinder further comprising:
   a toroidal mixing element slidably movable against the interior surface of the cylindrical tube and within the sample chamber between the piston and the sample end cap, the mixing element having an outer surface with a diameter slightly less than the inner diameter of the tube, and further having a passageway through the mixing element substantially coaxial with the axis of the sample cylinder for receiving and mixing the fluid sample in the sample chamber when the mixing element is moved between the piston and the sample end cap without affecting the volume of the sample chamber; and
   a projection member secured to and movable with the piston, the projection member extending from the sample facing surface of the piston toward the sample end cap and substantially filling the passageway in the mixing element when the sample chamber is empty.

2. The sample cylinder as defined in claim 1, wherein the toroidal mixing element has a planar piston facing surface and a planar opposing surface each perpendicular to the sample cylinder axis, and the passageway through the mixing element is a cylindrical-shaped passageway having a diameter in the range from 5% to 15% of the outer diameter of the mixing element.

3. The sample cylinder as defined in claim 1, wherein;
   the passageway through the mixing element has a cylindrical configuration of a substantially uniform diameter in the range of from 20% to 35% of the outer diameter of the mixing element; and
   the projection member on the piston has a cylindrical configuration of a substantially uniform diameter slightly less than the diameter of the passageway, and has a length approximating that of the passageway.

4. The sample cylinder as defined in claim 1, wherein the mixing element further comprises:
   a mixing element body;
   a mixing element end cap removably secured to the mixing element body; and
   an elastomeric ring secured between the body and the mixing element end cap and having a diameter slightly greater than the diameter of both the mixing element body and the mixing element end cap for slidable engaagement within the tube.

5. The sample cylinder as defined in claim 1, wherein the piston further comprises:
   a piston body;
   a first annular piston seal carried on the piston body for sealing with the tube and being sealing responsive to fluid pressure in the sample chamber;
   a second annular piston seal carried on the piston body for sealing engagement with tube and being sealingly responsive to fluid pressure in the charge chamber; and
   adjustment means for selectively adjusting the sealing effectiveness of the first and second piston seals.

6. The sample cylinder as defined in claim 5, wherein the adjustment means comprises;
   an axially compressible annular member associated with each of the first and second piston seals;
   a compression ring for moving axially to compress the annular members; and
   an axially centered adjustment bolt for axially moving the compression ring.

7. The sample cylinder as defined in claim 1, further comprising:
   a magnetic trip flag assembly external of the tube;
   a magnet carried on the piston for activating the magnetic trip flag assembly; and
   an elastomeric protector ring radially external of the magnet for preventing magnet fragments from contacting the tube.

8. The sample cylinder as defined in claim 1, further comprising:
   a housing secured to the charge end cap and having a passageway in fluid communication with the charge chamber via the charge port;
   a sight glass sealingly secured to the housing along a portion of the fluid passageway and having an exposed portion; and
   a coiled tape mounted to the housing and having one end extending through the charge end cap and secured to the piston, such that the axial position of the piston within the tube may be determined by viewing the tape through the sight glass.

9. The sample cylinder as defined in claim 8, wherein the entirety of the coiled tape is in fluid communication with the passageway through the housing and the charge chamber, and is sealed from the atmosphere.

10. The sample cylinder as defined in claim 1, further comprising:
valve means at one end of the cylindrical tube and secured to the sample end cap for controlling sample fluid flow to and from the sample chamber;
sensor means at the one end of the cylindrical tube and secured to the sample end cap for sensing fluid pressure in the sample chamber; and
a metallic protector removably fixed to the sample end cap for at least substantially enclosing the valve means and the sensor means and protecting the valve means and sensor means from damage during shipment of the sample cylinder.

11. A sample cylinder as defined in claim 1, wherein the outer surface of the toroidal mixing element is in sliding engagement with the interior surface of the cylindrical tube.

12. A sample cylinder as defined in claim 1, wherein the outer surface of the toroidal mixing element has a cylindrical configuration.

13. In a portable sample cylinder for collecting and transporting a fluid sample, including a cylindrical tube having an inner diameter and defining a sample cylinder axis, a sample end cap at one end of the tube and a charge end cap at the other end of the tube, a piston having a sample facing surface and a charge facing surface and slidable within the tube for defining a sample chamber between the sample end cap and the piston, and a charge chamber between the charge end cap and the piston, a sample input port in the sample end cap for introducing the fluid sample to the sample chamber, and a charge port in the charge end cap for inputting and releasing gas from the charge chamber, the piston further comprising:
a piston body;
a piston end cap carried by and axially movable with respect to the piston body;
adjustment means axially centered with respect to the piston body for controlling the axial position of the piston end cap relative to the piston body;
annular compressible sealing means carried on the piston body for sealing engagement with the tube;
a ring member axially movable by the piston end cap for exerting axially-directed pressure on the annular compressible sealing means such that increased axially directed pressure on the annular compressible means increases the sealing effectiveness of the sealing means.

14. The portable sample cylinder as defined in claim 13, wherein the adjustment means comprises:
a bolt threaded to the piston body for moving the piston end cap axially with respect to the piston body.

15. The portable sample cylinder as defined in claim 13, wherein the annular compressible sealing means comprises:
a first piston seal carried on the piston body for sealing with the tube and being sealingly responsive to fluid pressure in the annular compressible sample chamber; and
a second piston seal carried on the piston body for sealing engagement with tube and being sealingly responsive to fluid pressure in the charge chamber.

16. The portable sample cylinder as defined in claim 15, wherein the annular compressible sealing means further comprises:
each of the first and second piston seals has a general L-shaped cross-sectional configuration with an outward leg portion; and
first and second elastomeric rings each positioned radially inwardly of the corresponding leg portion of its respective L-shaped piston seal.

17. The portable sample cylinder as defined in claim 13, further comprising:
magnet means carried on the piston; and
an elastomeric protector ring means radially external of the magnet means for preventing any magnet means fragments from contacting the tube.

18. In a portable sample cylinder for collecting and transporting a fluid sample, including a cylindrical tube having an inner diameter and defining a sample cylinder axis, a sample end cap at one end of the tube and a charge end cap at the other end of the tube, a piston having a sample facing surface and a charge facing surface and slidable within the tube for defining a sample chamber between the sample end cap and the piston, and a charge chamber between the charge end cap and the piston, a sample input port in the sample end cap for introducing the fluid sample to the sample chamber, and a charge port in the charge end cap for inputting and releasing gas from the charge chamber, the piston further comprising;
a piston body;
a piston end cap carried by and axially movable with respect to the piston body;
an adjustment bolt threaded to the piston body for moving and selectively controlling the axial position of the piston end cap relative to the piston body, the adjustment bolt being axially centered with respect to the piston body;
sealing means carried on the piston body for sealing engagement with the tube;
a magnet secured into engagement with the piston body and the piston end cap by the adjustment bolt such that the adjustment bolt exerts an axially compressive force on the magnet; and
an elastromeric protector radially external of the magnet for sealingly preventing magnet fragments from contacting the tube.

19. The portable sample cylinder as defined in claim 18, wherein the elastomeric protector comprises a protector ring sealingly positioned between the piston body and the piston end cap.

20. The portable sample cylinder as defined in claim 18, further comprising:
a ring member axially movable by the piston end cap for exerting axial pressure on the sealing means such that increased axially directed pressure on the sealing means increases the sealing effectiveness of the sealing means.

* * * * *